United States Patent
Minagi et al.

(10) Patent No.: US 7,806,687 B2
(45) Date of Patent: Oct. 5, 2010

(54) OCCLUSAL STATE CORRECTION-SUPPORTING APPARATUS, PROGRAM, AND RECORDING MEDIUM

(75) Inventors: Shogo Minagi, Okayama (JP); Kazuhiro Oki, Kurashiki (JP)

(73) Assignee: National University Corporation Okayama University, Okayami-shi (JP)

( * ) Notice: Subject to any disclaimer, the term of this patent is extended or adjusted under 35 U.S.C. 154(b) by 123 days.

(21) Appl. No.: 11/990,209

(22) PCT Filed: Aug. 18, 2006

(86) PCT No.: PCT/JP2006/316260

§ 371 (c)(1),
(2), (4) Date: Feb. 25, 2008

(87) PCT Pub. No.: WO2007/021007

PCT Pub. Date: Feb. 22, 2007

(65) Prior Publication Data

US 2008/0311537 A1    Dec. 18, 2008

(30) Foreign Application Priority Data

Aug. 19, 2005    (JP)    ............... 2005-238714

(51) Int. Cl.
*A61C 3/00*    (2006.01)
(52) U.S. Cl. .................. 433/24; 433/213; 433/214; 382/128
(58) Field of Classification Search ........... 433/24, 433/213, 214; 700/108, 110; 382/128
See application file for complete search history.

(56) References Cited

U.S. PATENT DOCUMENTS

| 5,605,459 | A | 2/1997 | Kuroda et al. |
| 6,726,478 | B1 * | 4/2004 | Isiderio et al. ............... 433/69 |
| 2004/0259057 | A1 | 12/2004 | Kim |

FOREIGN PATENT DOCUMENTS

| JP | A 6-86717 | 3/1994 |
| JP | A 6-254108 | 9/1994 |
| JP | A 6-269468 | 9/1994 |
| JP | A 7-141529 | 6/1995 |
| JP | A 7-308329 | 11/1995 |

(Continued)

*Primary Examiner*—Cris L Rodriguez
*Assistant Examiner*—Eric Rosen
(74) *Attorney, Agent, or Firm*—Oliff & Berridge, PLC

(57) ABSTRACT

An occlusal state correction-supporting apparatus, a program therefor, and a recording medium thereof are provided, which can generate necessary, effective information in order to complete the shape of teeth excellently bitten. A shape-extracting means 10 extracts and stores shaped data of an upper jaw and a lower jaw. A position-extracting means 20 extracts and stores absolute coordinate data of reference points. A condition setting and distance-computing means 30 computes the distance between a upper jaw model 100 and a lower jaw model 200 while gradually bringing them close in a perpendicular direction. The condition setting and distance-computing means 30 also sets a condition of occlusal contact point, executes such approach movement again, and computes the distance. A correction area and amount-determining means 40 obtains information through a operator's operation, which indicates that desired occlusal state has been obtained, and determines the correction area and the correction-amount based on the occlusal state of the upper jaw and the lower jaw at that time.

8 Claims, 6 Drawing Sheets

FOREIGN PATENT DOCUMENTS

| | | |
|---|---|---|
| JP | A 8-280715 | 10/1996 |
| JP | A 2001-112743 | 4/2001 |
| JP | A 2002-526155 | 8/2002 |
| JP | A 2002-336282 | 11/2002 |
| JP | A 2002-355264 | 12/2002 |
| JP | A 2004-500149 | 1/2004 |
| JP | A 2004-81865 | 3/2004 |
| JP | A 2004-167032 | 6/2004 |
| JP | A 2004-195151 | 7/2004 |
| JP | A 2004-229943 | 8/2004 |
| JP | A 2005-87646 | 4/2005 |
| JP | A 2005-185767 | 7/2005 |
| WO | WO 03/037204 A1 | 5/2003 |

* cited by examiner

OCCLUSAL STATE CORRECTION-SUPPORTING APPARATUS, PROGRAM, AND RECORDING MEDIUM

TECHNICAL FIELD

The present invention relates to the technology that simulates occlusal state correction using the dentiform. In particular, the present invention relates to an apparatus for supporting of occlusal state correction, a program therefor and a recording medium thereof, which generate the information necessary to achieve an excellent occlusal state correction.

RELATED ART

For the treatment of the jaw deformity, the treatment plan is generally made before jaw surgery by using the three-dimensional bone model made by the bone image, the X-ray photograph or lithography technique which are three-dimensionally constructed with CT, MRI, and so on, and then the operation contents are determined. Then, the occlusal state is adjusted to improve occlusion of teeth after jaw surgery. In this case, if before jaw surgery the occlusal state after said jaw surgery can be expected, the appropriate jaw surgery can be executed under an appropriate treatment plan. However, it was difficult to expect the postoperative position and shape of each tooth before jaw surgery conventionally, and to expect the occlusal state to which the contact relation between teeth of an upper and lower jaws is determined.

To deal with this problem, one technique is disclosed in the patent document 1, Japanese Patent Application Laid-Open No. 1994-269568. For example, an articulator that simulates the occlusal state of teeth is used to obtain the measurement result of the occlusal state of teeth, and a three-dimensional position relation of the lower jaw with respect to the brainpan or certain reference position is measured based on said measurement result, and the result is displayed. This enables the correction treatments of teeth by overlapping and displaying in the CRT the image data of the three-dimensional position relation of the lower jaw bone and the data that indicates most naturally, substantially ideal occlusal state of teeth, without the judgment of dentist individual's capability and feeling.

Moreover, systems for gradually relocating of teeth to an appropriate position are disclosed in the patent document 2, Japanese Patent Application Laid-Open No. 2004-500149, and the patent document 3, Japanese Patent Application Laid-Open No. 2002-526155. The system of the patent document 2 prepares the arch form representative of the arrangement of teeth, arranges plural teeth according to this arch form, determines the distance difference between each tooth and the adjoining teeth, and moves each tooth according to the distance difference. The system of patent document 3 displays information concerning chew to fit for upper and lower teeth in the masticatory system, and determines the occlusal position of the teeth based on chosen instruction.

Moreover, a jaw movement-measuring apparatus that detects the position of the upper jaw and the lower jaw, measures relative movement tracks, and executes the occlusal state simulations of teeth is disclosed in the patent documents 4-13, Japanese Patent Application Laid-Open No. 2004-229943, No. 2004-195151, No. 2004-167032, No. 2004-81865, No. 2002-355264, No. 2002-336282, No. 2001-112743, No. 1995-308329, No. 1994-254108 and No. 1994-86717.

[Patent document 1] Japanese Patent Application Laid-Open No. 1994-269468

[Patent document 2] Japanese Patent Application Laid-Open No. 2004-500149

[Patent document 3] Japanese Patent Application Laid-Open No. 2002-526155

[Patent document 4] Japanese Patent Application Laid-Open No. 2004-229943

[Patent document 5] Japanese Patent Application Laid-Open No. 2004-195151

[Patent document 6] Japanese Patent Application Laid-Open No. 2004-167032

[Patent document 7] Japanese Patent Application Laid-Open No. 2004-81865

[Patent document 8] Japanese Patent Application Laid-Open No. 2002-355264

[Patent document 9] Japanese Patent Application Laid-Open No. 2002-336282

[Patent document 10] Japanese Patent Application Laid-Open No. 2001-112743

[Patent document 11] Japanese Patent Application Laid-Open No. 1995-308329

[Patent document 12] Japanese Patent Application Laid-Open No. 1994-254108

[Patent document 13] Japanese Patent Application Laid-Open No. 1994-86717

DISCLOSURE OF THE INVENTION

Problems to be Solved by the Invention

However, when the occlusal state by which the position of each tooth, shape thereof, and the contact relation of teeth in upper and lower jaws, after said jaw surgery are determined is expected before jaw surgery, enough information could not be necessarily obtained in the above-described technique.

Therefore, the present invention is provided to solve the above-described problem. The purpose of the present invention is to be provided with an occlusal state correction-supporting apparatus, a program therefor and a recording medium thereof. Thereby, necessary, effective information may be generated to complete the shape of teeth excellently bitten.

Means for Solving the Problem

According to the present invention, there is provided an occlusal state correction-supporting apparatus for generating of information necessary to correct the tooth arrangement surgically. The apparatus comprise a means for extracting the shape data of an upper jaw and an lower jaw; a means for specifying position data of occlusal part of the upper jaw and the lower jaw; a means for moving at least one of the upper jaw and the lower jaw, and computing the distance between occlusal parts based on the position data; a means for stopping said movement, when determining that each occlusal-part is respectively contacted based on the calculated distance a means for setting the condition of allowable cut of part of the occlusal contact; a means for proceeding the movement, if setting of the condition of allowable cut of part of the occlusal contact has been done; and a means for determining the correction area and the correction-amount of teeth according to occlusal state of the upper jaw and the lower jaw at the time of stopping of the movement. Thereby, the operator (surgeon) may verify the correction area and the correction-amount of teeth, and obtain necessary, effective information to complete the shape of teeth excellently bitten.

Moreover, the occlusal state correction-supporting apparatus according to the present invention further comprises a means for displaying into a display screen the determined correction area and the determined correction amount of teeth, and the shape of the upper and lower jaws. In addition, the occlusal state correction-supporting apparatus according to the present invention further comprises a means for calculating of area of each occlusal part of the upper and lower jaws in the determined correction area of teeth, and providing into the display screen said area together with the determined correction area and the determined correction amount of teeth, and the shape of the upper and lower jaws.

Preferably, the occlusal state correction-supporting apparatus according to the present invention further comprises a means for stopping said movement, if it is determined that each occlusal part has come in contact, and then proceeding the movement after setting the condition of allowable cut of part of the occlusal contact.

Moreover, in the occlusal state correction-supporting apparatus according to the present invention, setting the allowable cutting condition of each area of occlusal part of the upper and lower jaws. In addition, in the occlusal state correction-supporting apparatus according to the present invention, a maximum allowable cut value is set as another condition of part of the occlusal contact instead of the condition of allowable cut.

Moreover, in the occlusal state correction-supporting apparatus according to the present invention, the distance between occlusal parts is computed based on a positional coordinate data of the occlusal part of the upper jaw and the lower jaw, the positional coordinate data being specified from the positional coordinate data of at least three reference points in the upper jaw and the lower jaw, respectively.

Moreover, in the occlusal state correction-supporting apparatus according to the present invention, the correction area is part of occlusal contact set for the condition of the allowable cut if the movement is proceeded over said contact part and then stopped, and is an area overlapped between the upper jaw and the lower jaw; and the correction-amount is a distance from said contact part to the part where the movement is proceeded and then stopped.

Moreover, in the occlusal state correction-supporting apparatus according to the present invention further comprises a means for removing the shape data of the determined correction area from the shape data of the upper jaw and the lower jaw, and newly generating an upper jaw data and a lower jaw data.

An occlusal state correction-supporting program according to the present invention, the program for generating of information necessary to correct the tooth arrangement surgically, the program including processing procedure to be executed in a computer provided for an occlusal state correction-supporting apparatus, the processing procedure comprise the steps of extracting the shape data of an upper jaw and an lower jaw; specifying position data of occlusal part of the upper jaw and the lower jaw; moving at least one of the upper jaw and the lower jaw, and computing the distance between occlusal parts based on the position data; stopping said movement, if it is determined that depending to the computed distance each occlusal part has come in contact; setting the condition of allowable cut of part of the occlusal contact; proceeding the movement, if setting of the condition of allowable cut of part of the occlusal contact has been done; and determining the correction area and the correction-amount of teeth according to occlusal state of the upper jaw and the lower jaw at the time of stopping of the movement.

By the way, while extracting the upper jaw and the lower jaw to specify the position data of each occlusal part of the upper jaw and the lower jaw is not the feature of the present invention, providing the mechanism for determining the correction area and the correction-amount is the feature of the present invention. The jaw movement-measuring apparatus measures the shape data of the upper jaw and the lower jaw, and measures the position data of the occlusal state, as described in the above-described patent documents. The feature of the present invention is to determine the correction area and the correction-amount of the teeth using said extracted data by the jaw movement-measuring apparatus.

EFFECT OF THE INVENTION

According to the present invention, the upper and the lower jaws are moved, the distance of each occlusal part is calculated, and the correction area and the correction-amount of teeth are determined. As a result, this enables to generate effective information needed to complete the better shape of teeth bitten. For example, this enables to obtain information for adjusting the occlusal state of teeth before jaw surgery.

DESCRIPTION OF THE NUMERALS

Figure 1:
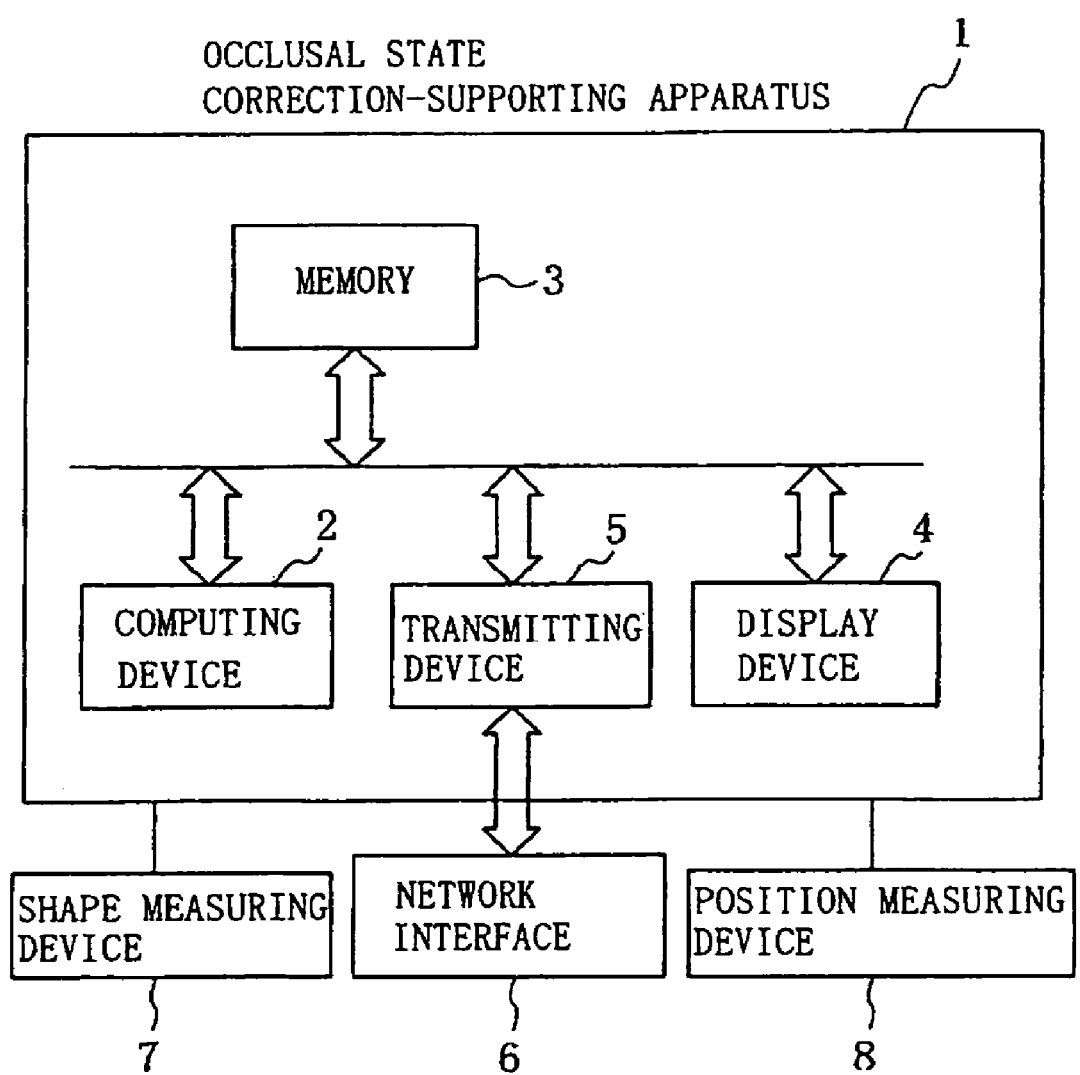
FIG. 1 is a block diagram showing the hardware arrangement of an occlusal state correction-supporting apparatus by an embodiment in accordance with the present invention.

1 Occlusal state correction-supporting apparatus
2 Computing device
3 Memory device
4 Display device
5 Transmitting device
6 Network interface
7 Shape-measuring device
8 Position measuring device
10 Shape-extracting means
20 Position-extracting means
30 Condition setting and distance-computing means
40 Correction area and amount-determining means
100 Upper jaw model
110 Arch for upper jaw
120,130,140 Upper jaw's reference point
200 Lower jaw model
210 Arch for lower jaws
220,230,240 Lower jaw's reference point

BEST MODE FOR CARRYING OUT THE INVENTION

Hereinafter, an embodiment of the present invention will be described in detail with reference to drawings.

[Arrangement]

FIG. 1 is a block diagram showing the hardware arrangement of an occlusal state correction-supporting apparatus by an embodiment in accordance with the present invention. This occlusal state correction-supporting apparatus 1 comprises a computing device 2 for inputting a data from a shape-measuring device 7 and a position measuring device 8 to carry out data processing depending on a program; a memory device 3 for storing the program and the data; a display device 4 for displaying of processing result computed by the computing device 2 and of data operated by an operator into the display screen; and a transmitting device 5 for sending and receiving of the data through a network interface 6 that is connected to external network (not shown), such as internet. The computing device 2 inputs the operating data from a mouse and a keyboard (not shown) by the operator, executes the program and the data read from the memory device 3 according to the operation of the operator, and provides the execution result to display in the display device 4. That is, the computing device 2 reads a correction-supporting program described for a series of processing, as described later, from the memory device 3 with CPU, develops and executes the correction support program on RAM, and stores the executed result into the memory device 3, or provides the executed result to display in the display device 4.

Figure 2:
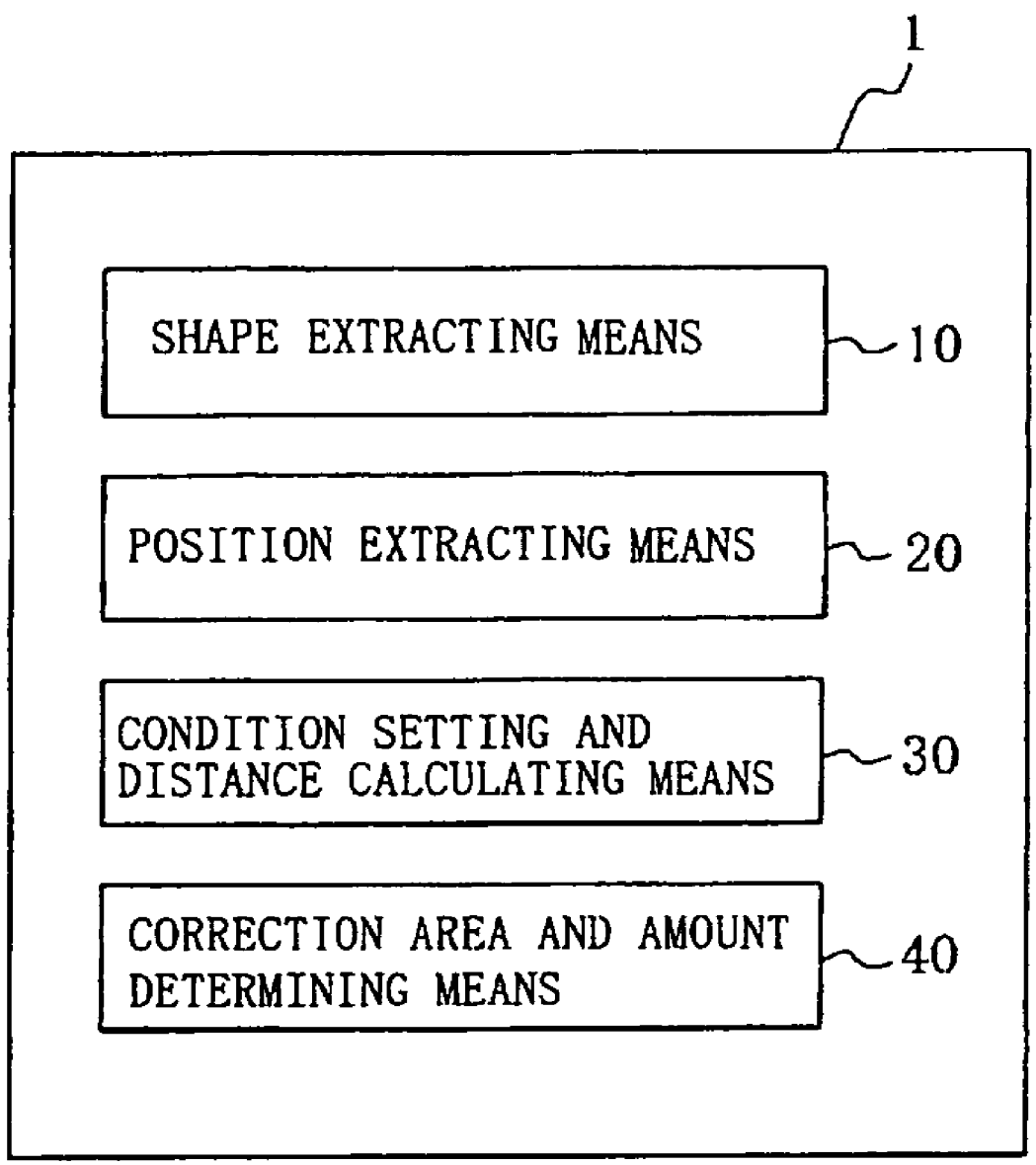
FIG. 2 is a block diagram showing the function arrangement of an occlusal state correction-supporting apparatus by an embodiment in accordance with the present invention.

FIG. 2 is a block diagram showing the function arrangement of an occlusal state correction-supporting apparatus by an embodiment in accordance with the present invention. This occlusal state correction-supporting apparatus 1 includes a shape-extracting means 10, a position-extracting means 20, a condition setting and distance-computing means 30, and a correction area and amount-determining means 40. Relating to the hardware elements shown in FIG. 1, these means read the correction-supporting program from the memory device 3, and execute each processing with the computing device 2.

Figure 3:
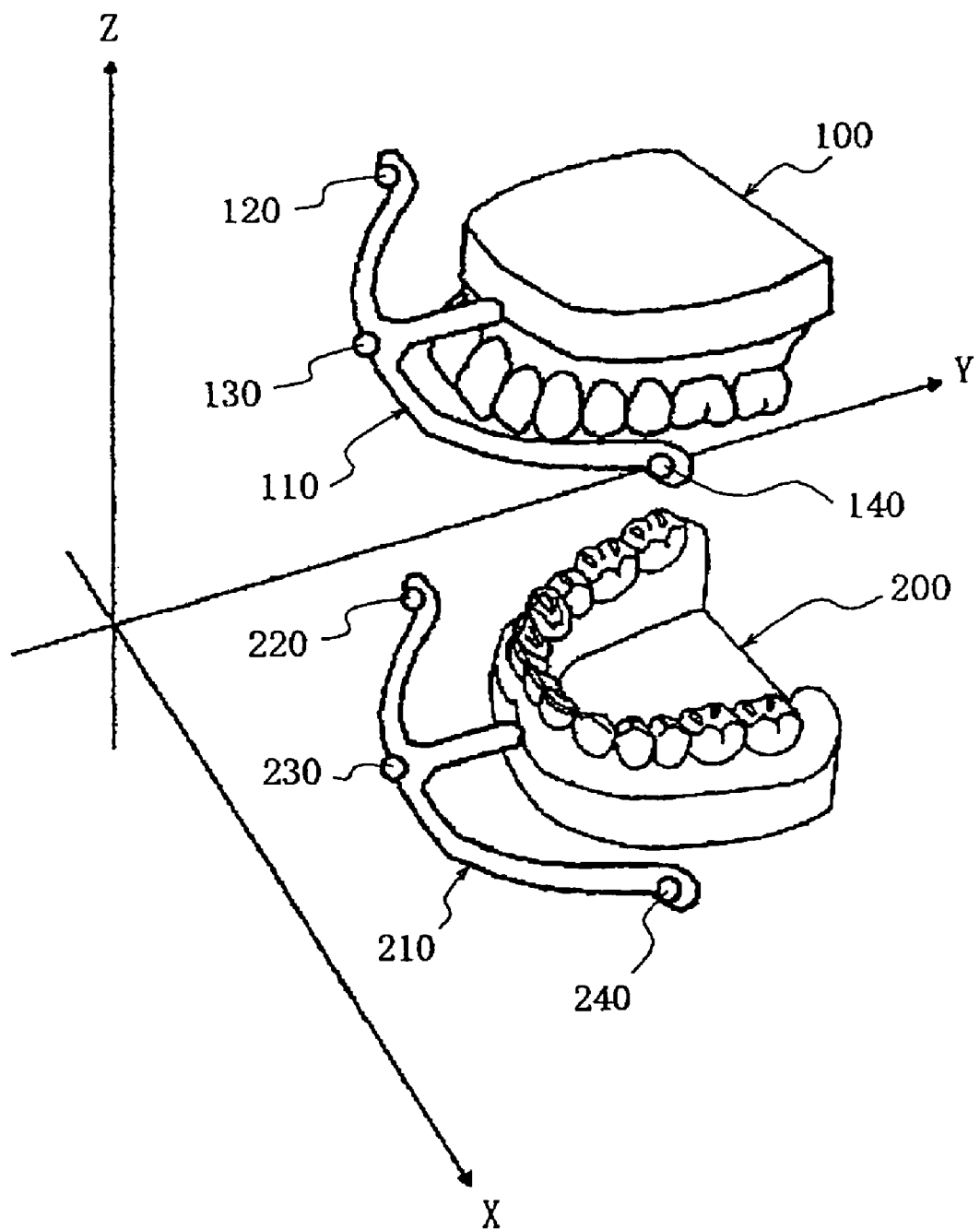
FIG. 3 is a diagram showing an upper jaw model and a lower jaw model to be described.

The shape-extracting means 10 extracts the upper jaw shape data and the lower jaw shape data from the shape-measuring device 7, and stores these data in the memory device 3. FIG. 3 is a diagram showing an upper jaw model and a lower jaw model to be described. In FIG. 3, an upper jaw model 100 comprises an arch for upper jaw 110 having upper jaw's reference points 120, 130 and 140 on the front side of the upper jaw model, and a lower jaw model 200 also comprises an arch for lower jaw 210 having lower jaw's reference points 220, 230 and 240 on the front side of the lower jaw model. These upper jaw's reference points 120, 130 and 140 and lower jaw's reference points 220, 230 and 240 of three points are reference points to specify coordinates of each part in an occlusal surface. That is, when coordinates of upper jaw's reference points 120, 130 and 140 are determined, coordinates of each part in an occlusal surface of the upper jaw model 100 may be specified. Similarly, when coordinates of lower jaw's reference points 220, 230 and 240 are determined, coordinates of each part in an occlusal surface of the lower jaw model 200 may be specified.

When an operator sets up the upper jaw model 100 in the shape-measuring device 7, the shape-measuring device 7 measures the upper jaw model 100, transforms to digital data, and generates an upper jaw shape data. Then, the shape-extracting means 10 extracts the upper jaw shape data from the shape-measuring device 7. Similarly, the shape-extracting means 10 extracts the lower jaw shape data, which is generated through the lower jaw model 200, from the shape-measuring device 7. In addition, the upper jaw shape data (or the lower jaw shape data) includes coordinate data (x, y, z) that indicates three-dimensional position of each part in an occlusal surface of the upper jaw (or lower jaw), and coordinate data (x, y, z) that indicates three-dimensional position of reference points 120, 130 and 140 (or 220, 230 and 240) in the upper jaw model 100 (or the lower jaw model 200). In this case, the data of each part in the occlusal surface and the data of the reference points are the data of a single coordinate system, and become basic data to determine coordinates of each part in the occlusal surface based on the upper jaw's reference points 120, 130 and 140 and the lower jaw's reference points 220, 230 and 240, if the upper jaw model 100 and the lower jaw model 200 are moved. That is, the shape-extracting means 10 extracts these data, and stores the coordinate data of three-dimensional position in the upper jaw's reference points 120, 130 and 140, and the relative coordinate data of three-dimensional position of each part in the occlusal surface with respect to the upper jaw's reference points 120, 130 and 140, for the upper jaw shape data of the upper jaw model 100. Moreover, the shape-extracting means 10 stores the coordinate data of three-dimensional position in the lower jaw's reference points 220, 230 and 240, and the relative coordinate data of three-dimensional position of each part in the occlusal surface with respect to the lower jaw's reference points 220, 230 and 240, for the lower jaw shape data of the lower jaw model 200. In addition, the relative coordinate data of three-dimensional position of each part in an occlusal surface is a group of three-dimensional coordinates value obtained by measuring the surface of form of teeth involved in the occlusal state of the upper jaw and the lower jaw.

For an example of the shape-measuring device 7 to be used here, there is a shape-measuring device of the contact type or a shape-measuring device of contactless type. The shape-measuring device of the contact type directly touches a measurement probe into the upper jaw model 100 and the lower jaw model 200 to measure the shape thereof. On the other hand, the shape measurement device of contactless type generates the shape data by irradiating laser beam to the upper jaw model 100 and the lower jaw model 200, and receiving its reflected light using light detecting elements of one-dimension such as CCD (Charge Coupled Device) or PSD (Position Sensing Device). Moreover, there is also a shape-measuring device to generate the shape data by irradiating zonal laser beam to the upper jaw model 100 and the lower jaw model 200, and receiving its reflected light using light detecting elements of two-dimensions.

In addition, the shape-measuring device 7 generating the upper jaw shape data and the lower jaw shape data is not limited by either a contact-type measurement device or a contactless-type measurement device. The shape-measuring device 7 may be a device that generates the upper jaw shape data and the lower jaw shape data from the upper jaw model 100 and the lower jaw model 200, and outputs (transmits) these data to the occlusal state correction-supporting apparatus 1.

If the operator installs the markers onto the upper jaw's reference points 120, 130 and 140 and the lower jaw's reference points 220, 230 and 240, and sets up the upper jaw model 100 and the lower jaw model 200 to the desired position of the position measuring device 8, the position-extracting means 20 extracts absolute coordinate data of the reference points, and stores said data in the memory device 3. Here, the absolute coordinate data of the reference points is data necessary to specify coordinate of the occlusal parts of the upper and lower jaws, and to calculate the distance between the occlusal parts of the upper and lower jaws by means of the condition setting and distance-computing means 30.

Specifically, if the operator sets the upper jaw model 100 and the lower jaw model 200 in which markers are installed at desired position, the position measuring device 8 sets the absolute coordinate system of X axis, Y axis, and Z axis as shown in FIG. 3, and generates absolute coordinate data (coordinate data in the absolute coordinate system) of the upper jaw's reference points 120, 130 and 140 and the lower jaw's reference points 220, 230 and 240. Thereby, since the shape of each occlusal surface of the upper and lower jaws has been made to digital data by the shape-measuring device 7, the relative position of said shape is determined using the reference points generated with position measuring device 8.

There are jaw movement-measuring devices of a motion capture type or six degree of freedom type as an example of positional measurement device 8 used here. The jaw movement-measuring device of the motion capture type may three-dimensionally capture a measurement object, in which the measurement object has a solid body on which some illuminant material or reflection material is attached in order to specify the position of the illuminant or the reflection body with at least two cameras. Then, the jaw movement-measuring device of the motion capture type specifies the position relation between two solid bodies, and provides relative positions, X, Y, Z, θx, θy, and θz, based on the other solid body, in which each of the measurement object has a solid body on which some illuminant material or reflection material at least three places of one solid body is attached. On the other hand, the jaw movement-measuring device of six degree of freedom may measure and observe the jaw movement, which is the relative movement between the upper jaw and the lower jaw, and outputs relative position of six degree of freedom X, Y, Z, θx, θy, and θz. In this case, it is desirable to measure each position of the tooth row of the upper jaw and the tooth row of the lower jaw, and to output relative position. In such a jaw movement-measuring device, there are a mechanical type, an optical type, a magnetic type, and a supersonic wave type. Thus, the position-measuring device 8 generates and outputs absolute coordinate data of the upper jaw's reference points 120, 130 and 140 and the lower jaw's reference points 220, 230 and 240.

The position measuring device 8 is not limited to the jaw movement-measuring device of the motion capture type or six degree of freedom type, and the position measuring device 8 may be such a device that generates relative position, X, Y, Z, θx, θy, and θz, of two solid bodies, and outputs (transmits) these data to the occlusal state correction-supporting apparatus 1.

The condition setting and distance-computing means 30 calculates the distance between the two jaw models while gradually bringing close the data of the upper jaw model 100 to the data of the lower jaw model 200 in the perpendicular direction (i.e. Z axis direction) from starting position, the starting position being specified as each position of the upper jaw model 100 and the lower jaw model 200 from absolute coordinate data of the upper jaw's reference points 120, 130 and 140 and the lower jaw's reference points 220, 230 and 240 extracted by means of the position-extracting means 20. Specifically, based on absolute coordinate data of the upper jaw's reference points 120, 130 and 140 and the lower jaw's reference points 220, 230 and 240 extracted by means of the position-extracting means 20 and the upper jaw shape data and the lower jaw shape data extracted by means of the shape-extracting means 10, the condition setting and distance-computing means 30 calculates absolute coordinate of each part of occlusal surface in the starting position. Then, if the data of the upper jaw model 100 and the data of the lower jaw model 200 are mutually gradually brought near in perpendicular direction (i.e. Z axis direction), the condition setting and distance-computing means 30 sequentially calculates the absolute coordinate of each part of the occlusal surface based on the absolute coordinate data of the reference points after being moved. Then, the condition setting and distance-computing means 30 calculates the distance between the two jaw models using the absolute coordinate of each part of the occlusal surface of said upper jaw and the absolute coordinate of each part of the occlusal surface of said lower jaw. Here, the approach movement manner to gradually bring close in the perpendicular direction should be preset by the operator's operation.

For instance, the case where only the lower jaw model 200 is moved for the approach movement is assumed. In this case, the condition setting and distance-computing means 30 calculates absolute coordinate data of the lower jaw's reference points 220, 230 and 240 after the approach movement. Then, the condition setting and distance-computing means 30 calculates the absolute coordinate of each part of the occlusal surface of said lower jaw after the approach movement based on the absolute coordinate data of the lower jaw's reference points 220, 230 and 240, using the stored absolute coordinate data of the lower jaw's reference points 220, 230 and 240 and the corresponding relative coordinate data of each part of the occlusal surface in the lower jaw. That is, the absolute coordinate of each part of the occlusal surface of said lower jaw may be specified using three absolute coordinate data of lower jaw's reference points 220, 230 and 240. Similarly, the absolute coordinate of each part of the occlusal surface of said upper jaw may be also specified using three absolute coordinate data of upper jaw's reference points 120, 130 and 140 after the approach movement. In this manner, the distance between two jaw models may be calculated.

In addition, the condition setting and distance-computing means 30 sets a "condition of occlusal contact point" through the operator's operation, and calculates the distance between two jaw models again while gradually bringing close the data of the upper jaw model 100 to the data of the lower jaw model 200 in the predetermined perpendicular direction. Moreover, the condition setting and distance-computing means 30 provides each shape of the upper jaw model 100 and the lower jaw model 200 and said calculated distance to display in the display device 4, using the upper jaw shape data and the lower jaw shape data extracted by means of the shape-extracting means 10.

Here, the "condition of occlusal contact point" means, for example, the following condition; if part of the occlusal surface may come in contact with part of the occlusal surface of the lower jaw over each area of tooth row of the occlusal surface of the upper jaw (i.e. the distance is equal to 0, or the distance is less than predefined value (to be defined as occlusal contact)), the condition of whether to bring them close in the perpendicular direction more, or in further approach movement the condition of maximum allowable distance (i.e. maximum allowable cut value). For the lower jaw, it is also similar. That is, for said condition, further approach movement may be set even if each occlusal part of the upper and lower jaws mutually comes in contact. Moreover, the maximum allowable distance may be set to do continuing the further approach movement from part of said occlusal contact. In this case, the operator may know the occlusal state of the upper jaw and the lower jaw at that time after said part will be cut down.

The operator may operate to set further another condition and perform said processing while referring to each shape of the upper jaw model 100 and the lower jaw model 200 displayed in the display device 4, and the distance calculated by the condition setting and distance-computing means 30. So, the operator may obtain desired occlusal state by repeating such a setting and processing.

If the operator obtains desired occlusal state, then the correction area and amount-determining means 40 determines the correction area and the correction-amount with respect to each occlusal surface of the upper jaw and the lower jaw. Specifically, the correction area and amount-determining means 40 may obtain information indicated that the operator has obtained desired occlusal state through the operator's operation; and then the correction area and amount-determining means 40 may determine the correction area and the correction-amount based on the occlusal state of the upper jaw and the lower jaw at that time, which is obtained from the correction area and amount-determining means 40.

Figure 4:
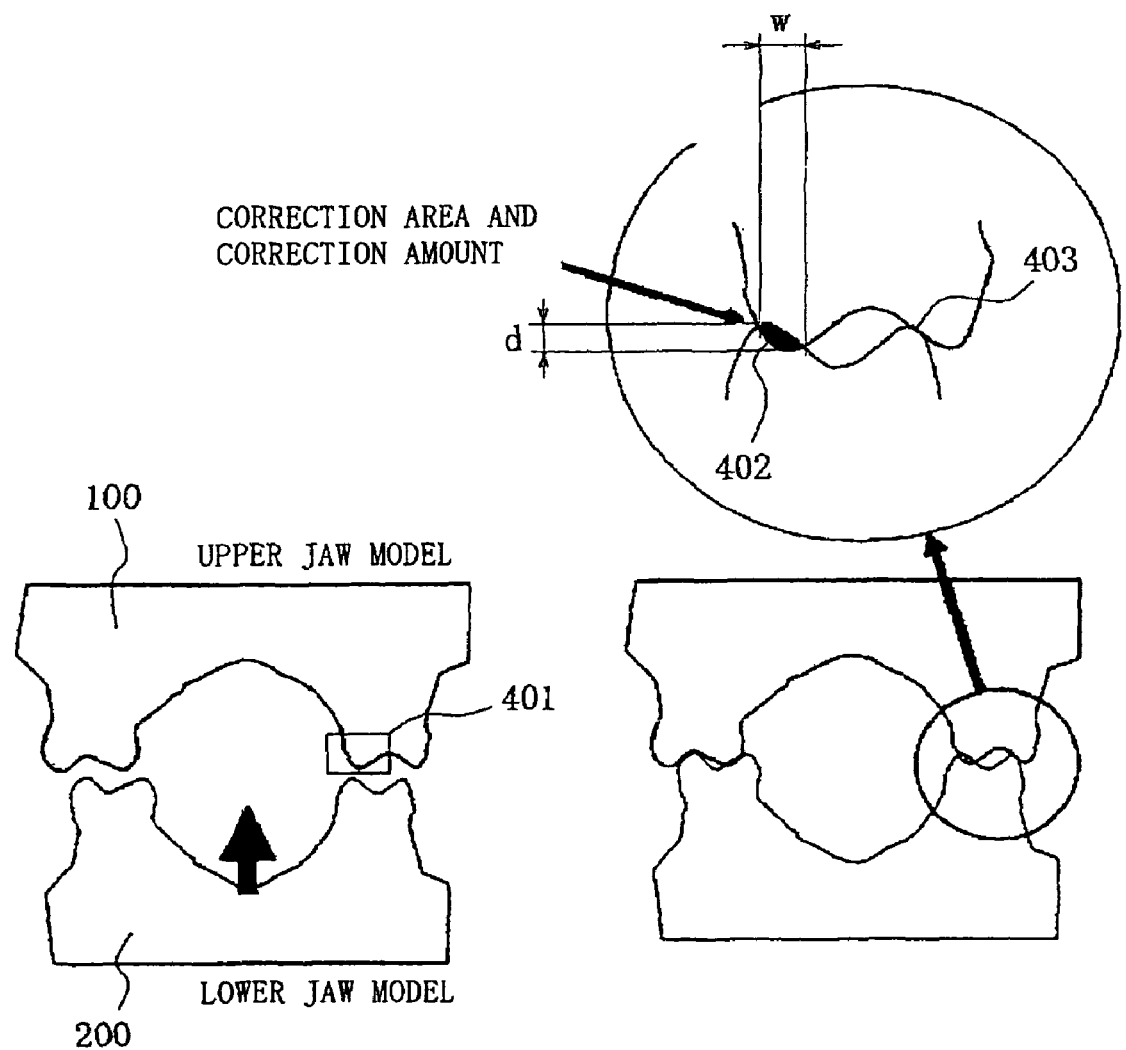
FIG. 4 is a flow chart showing the processing of a correction area and amount-determining means.

FIG. 4 is a flow chart showing the processing of a correction area and amount-determining means. For the condition of occlusal contact point in FIG. 4, said condition may be as follows: if part of the occlusal surface of one jaw comes in contact with part of the occlusal surface of the other jaw, these jaws should be moved more close, and the distance (i.e. the cut value (distance) of teeth to be cut) should be set. The condition setting and distance-computing means 30 calculates the distance between two jaw models again while gradually bringing close the data of the upper jaw model 100 and the data of the lower jaw model 200 in the predetermined perpendicular direction, and provides each shape of the upper jaw model 100 and the lower jaw model 200, and said calculated distance to display in the display device 4. Moreover, if the distance of each part of the occlusal surface in area 401 is equal to 0 or said distance is less than the predefined value, the condition setting and distance-computing means 30 determines that these jaws have come in contact. Then, the condition setting and distance-computing means 30 may bring more close these jaws in the perpendicular direction, because the predefined condition is to bring them close until a predetermined distance continuously. Then, if the distance of the occlusal part 403 is equal to 0 or said distance is less than the predefined value, the condition setting and distance-computing means 30 determines that these jaws have come in contact again. Then, the condition setting and distance-computing means 30 stops the approach movement, and provides each shape of the upper jaw model 100 and the lower jaw model 200 and the distance of each part at the stopped state to display in the display device 4. If the operator judges that desired occlusal state has been obtained, the correction area and amount-determining means 40 determines the correction area and the amount of correction based on the occlusal state of the upper jaw and the lower jaw in the stopped state, according to the operator's operation. In FIG. 4, the area 402 corresponds to the correction area, and at that time the distance d and width w correspond to the amounts of the correction. In addition, the correction area is area where the upper jaw model 100 and lower jaw model 200 overlap at the time of stopping after the approach movement has been continued over the part that comes in contact, and the correction-amount is the distance d and the width w of the overlapped area in the lower jaw model 200 with respect to the upper jaw model 100, as moved from the part that comes in contact to the position of stopping after the approach movement has been continued. This correction-amount has not to be limited to only the moved distance d and the width w, and the correction-amount may be a value of which the correction area is numerically representative.

In addition, if the distance of part of the occlusal surface in area 401 is identical with the maximum allowable cut value preset for a condition of the occlusal contact point, before the distance of part 403 of the occlusal surface becomes equal to 0, or the distance becomes less than predefined value, then the condition setting and distance-computing means 30 stops the approach movement, and provides information indicated that the approach movement has stopped to display.

[Operation]

Figure 5:
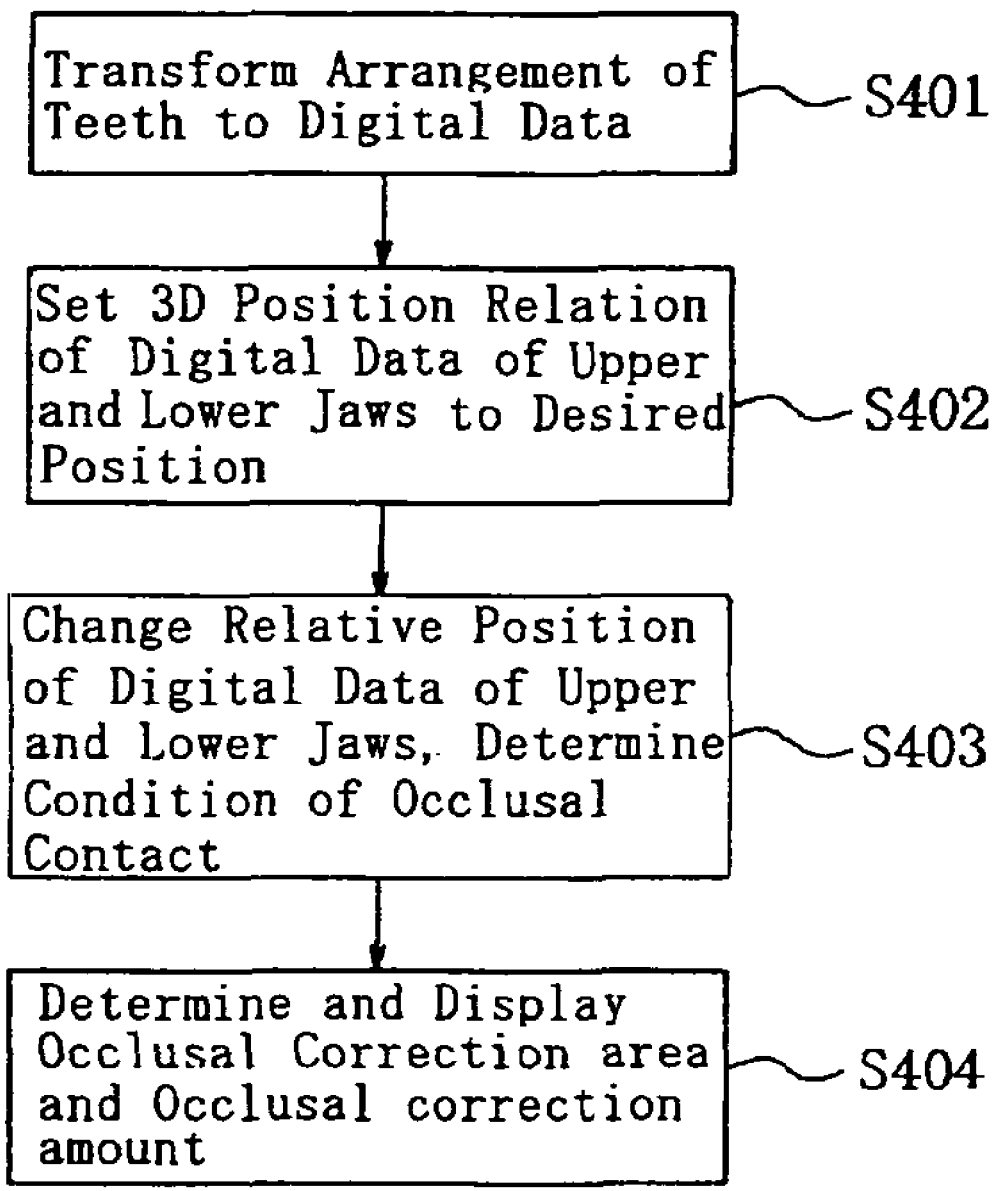
FIG. 5 is a flow chart showing the processing of the occlusal state correction-supporting apparatus of FIG. 2.

Then, the movement of the occlusal state correction-supporting apparatus 1 shown in FIG. 2 is described. FIG. 5 is a flow chart showing the processing of the occlusal state correction-supporting apparatus 1. The shape-extracting means 10 and the position-extracting means 20 transform the upper jaw model 100 and the lower jaw model 200 into digital data (step S401). Specifically, the shape-extracting means 10 extracts the upper jaw shape data of the upper jaw model 100 and the lower jaw shape data of the lower jaw model 200 from the shape-measuring device 7, and stores these data in the memory device 3. These upper jaw shape data and lower jaw shape data are used to calculate absolute coordinates of each part of occlusal surface when the upper jaw and lower jaw are moved, and to display each shape of jaw models into the display device 4.

The operator sets three-dimensional position relations of digital data of the upper and lower jaws at the position that the operator intends (step S402). Then, the position-extracting means 20 extracts the absolute coordinate data of the upper jaw's reference points 120, 130 and 140 and the absolute coordinate data of the lower jaw's reference points 220, 230 and 240 from the position measuring device 8. The absolute value coordinate data of these reference points is used to calculate the absolute coordinate of each part of occlusal surface when the upper jaw and the lower jaw are moved.

The condition setting and distance-computing means 30 may change the relative position of the digital data of the upper jaw model 100 and the lower jaw model 200 (step S403). In addition, the condition setting and distance-computing means 30 may set a condition of occlusal contact point depending on each area of each part of occlusal surface.

Then, if the operator could obtain desired occlusal state, then the correction area and amount-determining means 40 determines the correction area and the correction-amount and provides them to display in the display device 4 through the operator (step S404).

Figure 6:
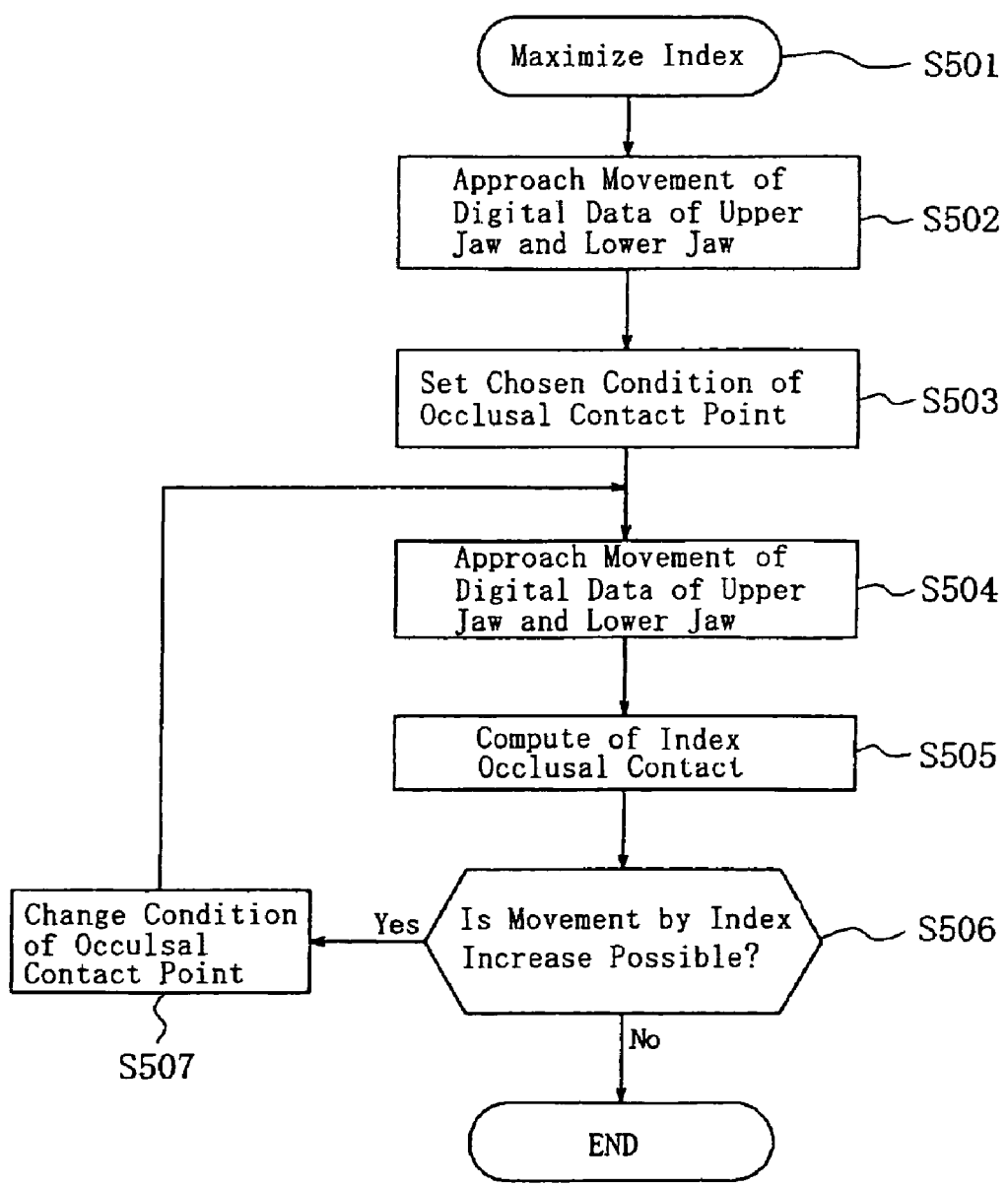
FIG. 6 is a flow chart showing the processing of a condition setting and distance-computing means.

Then, the operation of the condition setting and distance-computing means 30 shown in FIG. 2 is described. FIG. 6 is a flow chart showing the processing of the condition setting and distance-computing means 30. This flow chart shows a detailed procedure of processing about step 403 shown in FIG. 5. The condition setting and distance-computing means 30 maximizes the index that indicates the condition of occlusal contact point, which index indicates that the condition of occlusal contact point has not been set, (step S501). Then, the condition setting and distance-computing means 30 executes the approach movement between the digital data of the upper jaw and the digital data of the lower jaw (step S502), and stops the approach movement if the condition setting and distance-computing means 30 determines about the presence of the contact part that the distance of occlusal part becomes 0, or that the distance becomes less than predefined value.

If the operator set a condition of occlusal contact point (step S504), then the condition setting and distance-computing means 30 starts the approach movement again (step S504), and calculates the distance of occlusal part corresponding to the index of occlusal contact (step S505). Then, if the condition setting and distance-computing means 30 determines that the distance of the occlusal part becomes 0, or that the distance of the occlusal part (i.e. the distance in case of further approach movement over the contact point (where tooth will be cut)) is identical with the distance that is set as a condition of occlusal contact point through the approach movement, then the condition setting and distance-computing means 30 stops the approach movement. Then, the operator may determine whether new setting or change should be done (step S506). Then, the condition setting and distance-computing means 30 executes the processing for setting and changing of a condition of occlusal contact point through the operator's operation (step S506) and the processing is returned into the step S504, if the operator determines new setting or change. In this way, the correction area and amount-determining means 40 may determine the correction area and the correction-amount of occlusal state according to the flow charts shown in FIGS. 5 and 6.

Thus, according to one embodiment of the occlusal state correction-supporting apparatus 1 of the present invention, the condition setting and distance-computing means 30 gradually executes the approach movement between data of the upper jaw model 100 and data of the lower jaw model 200, calculates the distance between occlusal parts, and stops the approach movement if it is determined that the distance becomes 0 as each occlusal part have come in contact. Alternatively, the condition setting and distance-computing means 30 may set new condition of occlusal contact point through the operator's operation, execute further approach movement over the contact part according to the new condition, and stop the further approach movement if it is determined that the distance becomes 0 as each occlusal part have come in contact. Such approach movement and setting of condition of occlusal contact point may be repeated. Thus, the operator may obtain effective information to adjust occlusal state of tooth.

In this case, the occlusal state correction-supporting apparatus 1 may simulate jaw movement using the shape data of the upper jaw model 100 and the lower jaw model 200 extracted by the shape-extracting means 10, as well as using absolute coordinate data of reference points extracted by the position-extracting means 20. Moreover, the occlusal state correction-supporting apparatus 1 may extract the three-dimensional image data that constructs the bone shape of the patient captured by CT or MRI, match the coordinate system of the image data of said bone shape with the coordinate system of the shape data of the upper jaw model 100 and the lower jaw model 200 to integrate the shape data of the upper jaw model 100 and the skull data of the patient, or to integrate the shape data of the upper jaw model 100 and the bone data of the lower jaw, and thus simulate jaw movement.

Moreover, although it is described in this embodiment that the condition setting and distance-computing means 30 calculates the distance between two jaw models while gradually bringing close the data of the upper jaw model 100 and the data of the lower jaw model 200 in the perpendicular direction (i.e. Z direction), the condition setting and distance-computing means 30 may calculate the distance between two jaw models by moving both thereof in the horizontal direction (on the plane of XY), or rotating these jaw models on a horizontal plane. In addition, the condition setting and distance-computing means 30 may calculate the distance between two jaw models using the combination of the perpendicular movement, the horizontal migration, and the rotation movement. In this case, such movement type may be preset by the operator's operation.

Moreover, although it is described in this embodiment that the shape-measuring device 8 measures the shape of jaw models using three reference points of each of the upper jaw's reference points 120, 130 and 140 and the lower jaw's reference points 220, 230 and 240, and that the condition setting and distance-computing means 30 calculates the distance of each occlusal part of the upper jaw and the lower jaw based on said three reference points, the reference points has not to be limited to only three, and the reference points may be three or more.

Moreover, although it is described in this embodiment that the shape-extracting means 10 extracts the upper jaw shape data and the lower jaw shape data from the shape-measuring device 7, and that the position-extracting means 20 extracts absolute coordinate data of the reference points on the upper jaw model 100 and the lower jaw model 200, an alternative means of the shape-extracting means 10 and the position-extracting means 20 may collectively extract the upper jaw shape data, the lower jaw shape data and the reference points from a measuring device that involves each function of the shape-measuring means 7 and the position measuring means 8.

Moreover, although it is described in this embodiment that the condition setting and distance-computing means 30 provides each shape of the upper jaw model 100 and the lower jaw model 200 and the distance of occlusal part to display in the display device 4, and that the correction area and amount-determining means 40 provides the correction area and the correction-amount to display in the display device 4, these device may display the value of contact area between the upper jaw and the lower jaw. That is, the condition setting and distance-computing means 30 or the correction area and amount-determining means 40 may display the value of contact area where the upper jaw model 100 and the lower jaw model 200 overlap, such as contact area of the correction area 402 shown in FIG. 4, in the display device 4.

Moreover, although it is described in this embodiment that the correction area and amount-determining means 40 determines the correction area and the correction-amount, the correction area and amount-determining means 40 further may remove the shape data in the correction area of occlusal surface from the upper jaw shape data and the lower jaw shape data after determining the correction area and the correction-amount, and the correction area and amount-determining means 40 further may newly generate the upper jaw shape data and the lower jaw shape data on corrected base in order to store these newly generated upper jaw shape data and lower jaw shape data, and the correction-amount at that time in the memory device 3. The condition setting and distance-computing means 30 may calculate the distance between the two jaw models while gradually bringing close the data of the upper jaw model 100 and the data of the lower jaw model 200 in the perpendicular direction from new starting position using the upper jaw shape data and the lower jaw shape data on corrected base stored in the memory device 4 on the basis of absolute coordinate data of the reference points newly extracted by the position-extracting means 20. Thereby, each history of the upper jaw shape data and the lower jaw shape data on corrected base (the correction area has been cut) and each history of the correction-amount may be stored in the memory device 3.

Besides, the occlusal state correction-supporting apparatus 1 comprises a computing device 2; a memory device 3 that is a volatile storage media, such as RAM, or a nonvolatile storage media, such as ROM; an input device (not shown) that is a key board, a pointing device, or the like; display device 4 for displaying of the image or data; and a transmitting device for communicating over external networks. In this case, each function of the shape-extracting means 10, the position-extracting means 20, the condition setting and distance-computing means 30 and the correction area and amount-determining means 40, the each function being provided by the occlusal state correction-supporting apparatus 1, may be implemented by means of the computing device 2 for executing of programs described about these functions, respectively. Moreover, these programs may be distributed by using a storage media, such as a magnetic disk (Floppy disk, or Hard Disk etc.), an optical disk (CD-ROM or DVD, etc.), or a semiconductor memory, or the like.

The invention claimed is:

1. An occlusal state correction-supporting apparatus for generating information necessary to surgically correct a tooth arrangement, the apparatus comprising:
    a shape-extracting means for extracting shape data of an upper jaw and a lower jaw, the upper jaw being an upper jaw model including an arch for the upper jaw having at least three reference points on the front side of the upper jaw model, and the lower jaw being a lower jaw model including an arch for the lower jaw having at least three reference points on the front side of the lower jaw model;
    a point-extracting means for specifying position data of an occlusal part of the upper jaw and the lower jaw;
    a memory means for storing the shape data of each of the upper jaw and the lower jaw including data of each part of an occlusal surface of the upper jaw and the lower jaw, and data of each of the reference points, in order to specify the upper jaw model and the lower jaw model with predetermined positional coordinates in six degrees of freedom;
    a condition setting and distance-computing means for reading the shape data from the memory means, for moving at least one of the upper jaw model and the lower jaw model within the positional coordinates in the six degrees of freedom, for sequentially computing a distance between the occlusal parts of the upper jaw model and the lower jaw model as the distance between respective corresponding reference points based on the reference points of the upper jaw model and the lower jaw model, for stopping a calculation of the approach movement between jaw models, when determining that each occlusal part is respectively contacted based on the calculated distance when the computed distance is less than a predefined value, for setting an allowable cutting condition of each area of the occlusal part of the upper and lower jaws, for starting the approach movement after setting the allowable cutting condition of each area of the occlusal part of the upper and lower jaws and for stopping the approach movement, if the computed distance achieves a predetermined maximum allowable cut value, before the computed distance becomes less than the predefined value; and
    a correction area and amount-determining means for determining a correction area and a correction amount of teeth according to the occlusal state of the upper jaw and the lower jaw at the time of stopping of the approach movement.

2. The occlusal state correction-supporting apparatus according to claim 1, the apparatus further comprising:
    a computing device for displaying the determined correction area and the determined correction amount of teeth, and the shape of the upper and lower jaws onto a display screen.

3. The occlusal state correction-supporting apparatus according to claim 2, wherein the computing device calculates an area of the occlusal part of the upper and lower jaws in the determined correction area of teeth, and provides the calculated area together with the determined correction area and the determined correction amount of teeth, and the shape of the upper and lower jaws onto a display screen.

4. The occlusal state correction-supporting apparatus according to claim 1, wherein a maximum allowable cut value is set as another condition of part of the occlusal contact instead of the allowable cutting condition.

5. The occlusal state correction-supporting apparatus according to claim 1, wherein the distance between occlusal parts is computed based on positional coordinate data being specified from the positional coordinate data of the at least three reference points in the upper jaw and the lower jaw, respectively.

6. The occlusal state correction-supporting apparatus according to claim 1, wherein the correction area is part of an occlusal contact set for the condition of the allowable cut if the movement is proceeded over the contact part and then stopped, and is an area overlapped between the upper jaw and the lower jaw; and
    the correction amount is a distance from the contact part to a part where the approach movement between the jaw models is proceeded and then stopped.

7. The occlusal state correction-supporting apparatus according to claim 1, the apparatus further comprising:
    a shape data removal means for removing the shape data of the determined correction area from the shape data of the upper jaw and the lower jaw, and newly generating an upper jaw data and a lower jaw data.

8. A method of occlusal state correction-support for generating information necessary to surgically correct a tooth arrangement, the method comprising:
    extracting shape data of each of an upper jaw and a lower jaw using a computing device, the upper jaw being an upper jaw model including an arch for the upper jaw having at least three reference points on the front side of the upper jaw model, and the lower jaw being a lower jaw model including an arch for the lower jaw having at least three reference points on the front side of the lower jaw model;
    specifying position data of an occlusal part of the upper jaw and the lower jaw;
    storing onto a memory the shape data of each of the upper jaw and the lower jaw including data of the occlusal part of the upper jaw and the lower jaw, and data of each of the reference points in order to specify the upper jaw model and the lower jaw model with predetermined positional coordinates in six degrees of freedom;
    reading the shape data of each of the upper jaw and the lower jaw from the memory, moving at least one of the upper jaw model and the lower jaw model within the positional coordinates in six degrees of freedom, and sequentially computing, with the computing device, a distance between the occlusal parts of the upper jaw model and the lower jaw model as a distance between respective corresponding reference points based on the reference points of the upper jaw model and the lower jaw model;

stopping a calculation of the approach movement between the jaw models, when determining that each occlusal part is respectively contacted based on a calculated distance when the calculated distance is less than a predefined value;

setting an allowable cutting condition of the occlusal part of the upper and lower jaws;

starting an approach movement after setting the allowable cutting condition of the occlusal part of the upper and lower jaws;

stopping the approach movement, if the computed distance achieves a predetermined maximum allowable cut value, before the computed distance becomes less than the predefined value; and determining a correction area and a correction amount of teeth according to an occlusal state of the upper jaw and the lower jaw at the time of stopping of the approach movement.

* * * * *